United States Patent [19]

Matsuura

[11] Patent Number: 5,245,083
[45] Date of Patent: Sep. 14, 1993

[54] METHOD FOR PREPARING METHACROLEIN AND METHOD FOR PREPARING A CATALYST FOR USE IN THE PREPARATION OF METHACROLEIN

[75] Inventor: Ikuya Matsuura, Toyama, Japan

[73] Assignee: Mitsui Toatsu Chemicals, Inc., Tokyo, Japan

[21] Appl. No.: 841,510

[22] Filed: Feb. 26, 1992

[30] Foreign Application Priority Data

Feb. 27, 1991 [JP] Japan .................................. 3-032718

[51] Int. Cl.⁵ .............................................. C07C 45/34
[52] U.S. Cl. .................... 568/479; 568/471; 568/476
[58] Field of Search ............... 568/471, 473, 474, 476, 568/479, 475

[56] References Cited

U.S. PATENT DOCUMENTS

| | | |
|---|---|---|
| 3,497,461 | 2/1970 | McClellan et al. |
| 3,746,657 | 7/1973 | Miller et al. |
| 4,049,577 | 9/1977 | Childress et al. |
| 4,129,600 | 12/1978 | Childress et al. |
| 4,155,938 | 5/1979 | Yamamoto ................. 568/479 |
| 4,306,090 | 12/1981 | Kirch et al. ............. 568/479 |
| 4,354,044 | 10/1982 | Aoshima et al. .......... 568/471 |
| 4,388,223 | 6/1983 | Ferlazzo et al. |
| 4,511,671 | 4/1985 | Saito et al. |
| 5,138,100 | 8/1992 | Matsuura . |
| 5,144,090 | 9/1992 | Honda et al. |

FOREIGN PATENT DOCUMENTS

| | | |
|---|---|---|
| 0000835 | 2/1979 | European Pat. Off. |
| 0061830 | 6/1982 | European Pat. Off. |
| 0304867 | 1/1989 | European Pat. Off. |
| 1555679 | 11/1966 | France . |
| 2397229 | 2/1979 | France . |
| 48-52713 | 6/1973 | Japan . |
| 0016436 | 2/1981 | Japan .................... 568/479 |
| 1529384 | 10/1978 | United Kingdom . |

*Primary Examiner*—Werren B. Lone
*Attorney, Agent, or Firm*—Oblon, Spivak, McClelland, Maier & Neustadt

[57] ABSTRACT

A catalyst is herein disclosed, which comprises a mixture of a composition (1) represented by the following general formula (1):

$$(Mo)_a(Bi)_b(Fe)_c(X)_d(Z)_f(O)_g \qquad (1)$$

(wherein X represents one or both of Ni and Co, Z represents at least one element selected from the group consisting of W, Be, Mg, S, Ca, Sr, Ba, Te, Se, Ce, Ge, Mn, Zn, Cr, Ag, Sb, Pb, As, B, P, Nb, Cu, Cd, Sn, Al, Zr and Ti, a, b, c, d, f and g each represents an atomic ratio of each corresponding element and if a is assumed to be 12, b ranges from 0.1 to 10, c ranges from 0 to 20, d ranges from 0 to 20 and f ranges from 0 to 4 and g is a number of oxygen atom required for satisfying the valency requirement of the foregoing elements) and a composition (2) represented by the following general formula (2):

$$(A)_m(Mo)_n(O)_p \qquad (2)$$

(wherein A represents at least one element selected from K, Rb and Cs and m, n and p each represents an atomic ratio and if m is assumed to be 2, n ranges from 1 to 9 and p is 3n+1). The catalyst has improved activity, selectivity to methacrolein and stability and accordingly, methacrolein can be prepared, in good yield, by a gas-phase catalytic oxidation reaction of isobutylene or tertiary butanol with molecular oxygen through the use of the foregoing catalyst.

6 Claims, No Drawings

METHOD FOR PREPARING METHACROLEIN AND METHOD FOR PREPARING A CATALYST FOR USE IN THE PREPARATION OF METHACROLEIN

BACKGROUND OF THE INVENTION (a) Field of the Invention

The present invention relates to an improved method for preparing methacrolein through gas-phase catalytic oxidation of isobutylene or tertiary butanol with molecular oxygen and an improved method for preparing a catalyst for use in the catalytic oxidation reaction (b) Description of the Prior Art There have conventionally been proposed a variety of catalysts used in the preparation of methacrolein through gas-phase catalytic oxidation of isobutylene or tertiary butanol with molecular oxygen and, in particular, there have been many proposals concerning those comprising one or both of Co and Ni, and at least one element selected from the group consisting of K, Rb and Cs in addition to Mo, Bi and Fe as essential catalyst components among others In addition, there have recently been proposed those comprising an additional component such as Sb or Mg other than the foregoing catalyst components in order to enhance the quality of the catalysts (see, for instance, Japanese Unexamined Patent Publication (hereinafter referred to as "J.P. KOKAI") Nos. Sho 63-107745 and Sho 63-122642). However, these catalysts conventionally proposed are still insufficient in various catalytic properties such as catalytic activity, stability, lifetime and selectivity to methacrolein and there still remains room for further improvement.

SUMMARY OF THE INVENTION

Accordingly, an object of the present invention is to provide an improved method for preparing methacrolein, in good yield, through a gas-phase catalytic oxidation reaction of isobutylene or tertiary butanol with molecular oxygen in the presence of a catalyst which comprises a mixture of a composition comprising Mo, Bi and preferably at least one element selected from the group consisting of Fe, Ni and Co with a composition comprising an alkali metal salt of molybdic acid.

Another object of the present invention is to provide a method for preparing a catalyst for use in the foregoing method for preparing methacrolein, the catalyst being improved in catalytic activity, selectivity to methacrolein and stability, which comprises mixing a composition comprising Mo, Bi and preferably at least one element selected from the group consisting of Fe, Ni and Co with a composition comprising an alkali metal salt of molybdic acid, heating and mixing, evaporating to dryness and then firing the resulting mixture.

According to the present invention, there is provided a method for preparing methacrolein which comprises catalytically oxidizing, in a gas phase, isobutylene or tertiary butanol with molecular oxygen in the presence of a catalyst which comprises a mixture of a composition (1) represented by the following general formula (1):

$$(Mo)_a(Bi)_b(Fe)_c(X)_d(Z)_f(O)_g \tag{1}$$

(wherein X represents one or both of Ni and Co, Z represents at least one element selected from the group consisting of W, Be, Mg, S, Ca, Sr, Ba, Te, Se, Ce, Ge, Mn, Zn, Cr, Ag, Sb, Pb, As, B, P, Nb, Cu, Cd, Sn, Al, Zr and Ti, a, b, c, d, f and g each represents an atomic ratio of each corresponding element and if a is assumed to be 12, b ranges from 0.1 to 10, c ranges from 0 to 20, d ranges from 0 to 20 and f ranges from 0 to 4 and g is a number of oxygen atom required for satisfying the valency requirement of the foregoing elements) with a composition (2) represented by the following general formula (2):

$$(A)_m(Mo)_n(O)_p \tag{2}$$

(wherein A represents at least one element selected from K, Rb and Cs and m, n and p each represents an atomic ratio and if m is assumed to be 2, n ranges from 1 to 9 and p is 3n+1).

According to the present invention, there is also provided a method for preparing the foregoing catalyst for use in the aforementioned catalytic oxidation reaction, which comprises mixing the foregoing compositions (1) and (2), heating and mixing, evaporating the resulting mixture to dryness and firing the dried mixture.

DETAILED DESCRIPTION OF THE INVENTION

In the present invention, it is very important to obtain the catalyst used in the method of the present invention by separately preparing the foregoing compositions (1) and (2) and then admixing the compositions (1) and (2) thus separately prepared. This method for the preparation of the catalyst differs from the conventional catalyst of this kind which has been known in this field, but the overall composition of the resulting mixture is identical to that of the conventional catalyst. The catalyst of the present invention obtained by separately preparing the compositions (1) and (2) and then mixing them shows properties superior to those of the conventional catalyst though the overall compositions thereof are identical to one another. While the reason therefor has not yet been clearly elucidated, it can be considered that the compositions (1) and (2) each provides a plurality of preferred active sites required for the object reaction of the present invention and a high selectivity would be achieved due to the concerted effects of these active sites. On the other hand, in the conventional catalyst, the alkali metal elements in the composition (2) would form undesirable or unnecessary phases for the object reaction together with the elements as constituents of the composition (1) during preparation of the catalyst in particular, the precipitation process and accordingly, only a limited selectivity would be obtained.

Moreover, there is a preferable range of the mixing ratio of the composition (1) to the composition (2) in order to obtain desired effects of the present invention More specifically, these compositions are mixed so that the atomic ratio of K, Rb or Cs (component A) of the composition (2) to Bi of the composition (1) ranges preferably from 0.02 to 1.0 and more preferably from 0.05 to 0.5. This is because, if the atomic ratio is less than 0.02 or exceeds 1.0, the concerted effects obtained by combination use of composition (1) and composition (2) are insufficient and the selectivity and the oxidation activity of the resulting catalyst are insufficient.

The compositions (1) and (2) are prepared by any method currently employed in this field. For instance, they are prepared according to the following method.

The composition (1) can be prepared by dissolving an appropriate molybdate such as ammonium molybdate in pure water with heating, adding an aqueous solution of a Bi-containing compound to the resulting solution, optionally adding an aqueous solution of a compound of at least one element selected from Fe, Co and Ni, optionally adding a compound of at least one element selected from the group consisting of W, Be, Mg, S, Ca, Sr, Ba, Te, Se, Ce, Ge, Mn, Zn, Cr, Ag, Sb, Pb, As, B, P, Nb, Cu, Cd, Sn, Al, Zr and Ti, optionally adding a carrier such as $SiO_2$, followed by drying of the resulting slurry, calcination and firing at a temperature ranging from 200° to 650° C.

On the other hand, the composition (2) can be prepared by dissolving an appropriate molybdate such as ammonium molybdate in pure water with heating, adding a compound of at least one element selected from K, Rb and Cs, such as cesium nitrate so that the atomic ratio (Cs:Mo) is 2:1 to 2:9, neutralizing the mixture with nitric acid, followed by evaporation to dryness, calcination and firing at 200° to 500° C.

The catalyst of the present invention is prepared as follows. The foregoing compositions (1) and (2) are first mixed together so that the atomic ratio of K, Rb or Cs in the composition (2) to Bi in the composition (1) ranges from 0.02 to 1.0, preferably 0.05 to 0.5. At this stage, water is preferably added to the mixture for improving the quality of the resulting catalyst. The mixing process is performed at a temeprature ranging from 30° to 300° C. Then the resulting mixture is evaporated to dryness at a temperature of not more than 300° C. and fired at 300° to 650° C.

The amount of water added during mixing is not critical, but is selected so as to form a slurry which is effective for ensuring sufficient mixing of these compositions. Alternatively, when water is added, the mixing process can likewise be perfomed with heating in an autoclave under a self-generating pressure.

The catalyst is formed into granules or a molded body and used in a fixed bed, but may be used in a moving bed or a fluidized bed.

Ingredients for preparing the catalyst of the present invention are preferably compounds which can be decomposed into oxides during the process for preparing the catalyst. Such compounds include, for instance, nitrates, ammonium salts, salts with organic acids, oxides, metallic acid and ammonium salts of metallic acids.

Starting materials for silica as a carrier may be, for instance, silica sol, silica gel, silicic acid esters and silicates.

The gas-phase catalytic oxidation reaction according to the present invention is carried out by supplying, on the foregoing catalyst, a mixed gas comprising 1 to 10% by volume of isobutylene or tertiary butanol, 3 to 20% by volume of molecular oxygen and 70 to 96% by volume of a diluent gas at a temperature ranging from 250° to 450° C., a pressure ranging from ordinary pressure to 10 atm and a space velocity ranging from 300 to 5000/hr.

Air is generally used as a molecular oxygen source, but pure oxygen may likewise be used in the present invention.

Examples of the diluent gases are inert gases such as nitrogen gas and carbon dioxide gas. Alternatively, a part of an incondensable gas included in the reaction gas mixture may be circulated through the reaction system to use it as a diluent gas.

Water vapor is preferably used simultaneously with the diluent gas for improving the activity and selectivity of the catalyst used. In this case, the water vapor content in the starting gas mixture may in general be up to 60% by volume.

The present invention will hereinafter be explained in more detail with reference to the following working Examples and the effects practically accomplished by the present invention will also be discussed in detail in comparison with Comparative Examples.

EXAMPLE 1

There was dissolved, in 1200 ml of water, 127.2 g of ammonium paramolybdate under heating and stirring to give a solution (hereinafter referred to as "solution A"). Separately, 139.6 g of cobalt nitrate and 72.2 g of ferric nitrate were dissolved in 180 ml of water to give another solution (hereinafter referred to as "solution B"). Further, 28.6 g of bismuth nitrate was dissolved in an aqueous nitric acid solution comprising 15 ml of 60% nitric acid and 150 ml of water to give a solution (hereinafter referred to as "solution C"). Solution B and solution C were, in order, dropwise added to and mixed with solution A, the resulting slurry was spray-dried, then calcined and fired at 400° C. to give a composition (1) having an atomic ratio: Mo/Bi/Fe/Co of 12/1/3/8.

Ammonium molybdate (19.6 g) was dissolved in 200 ml of water under heating and stirring followed by addition of 39.0 g of cesium nitrate, neutralization of the mixture with nitric acid, evaporation to dryness, calcination and firing at 400° C. to give a composition (2) having an atomic ratio: Cs/Mo of 2/1.

The compositions (1) and (2) were mixed in a ratio of 116/1 so that the atomic ratio: Cs/Bi was equal to 0.1, then water was added in such an amount that the water content of the mixture was 80% by weight, the resulting mixture was sufficiently heated and mixed at 100° C., evaporated to dryness and fired at 400° C. to give a catalyst.

The catalyst (1 ml) thus prepared was charged in a flow reactor currently employed and a reaction was carried out at a reaction temperature of 340° C. and a space velocity of 3600/hr using a starting gas mixture which comprised 8.3% by volume of isobutylene, 16.7% by volume of oxygen, 8.3% by volume of water vapor and the balance (66.7% by volume) of nitrogen gas to evaluate the quality of the catalyst. The results thus obtained are listed in the following Table 1.

EXAMPLES 2 TO 9

Catalysts were prepared in the same manner used in Example 1 except that a composition (1) prepared by a method identical with that used in Example 1 and compositions (2) listed in Table 1 were used and that the atomic ratio: A/Bi (wherein A being the same as that defined above) was adjusted to each corresponding value listed in Table 1. The properties of the resulting catalysts were evaluated in the same manner used in Example 1. The results obtained are summarized in Table 1.

EXAMPLE 10

The same procedures used in Example 1 were repeated to give a catalyst except that 69.6 g of nickel nitrate was substituted for the cobalt nitrate used in Example 1. Then the properties of the resulting catalyst were evaluated in the same manner used in Example 1. The results obtained are summarized in Table 1.

EXAMPLES 11 AND 12

Catalysts were prepared in the same manner used in Example 10 except that a composition (1) prepared by a method identical with that used in Example 10 and compositions (2) listed in Table 1 were used and that each atomic ratio was adjusted to the corresponding value listed in Table 1. Then the properties of the resulting catalysts were evaluated in the same manner used in Example 1. The results obtained are summarized in Table 1.

EXAMPLE 13

The same procedures used in Example 1 were repeated to give a catalyst except that a composition (1) prepared by a method identical with that used in Example 1 and compositions (2) listed in Table 1 were used and that the atomic ratio: A/Bi was adjusted to 1.2. The properties of the resulting catalysts were evaluated in the same manner used in Example 1. The results obtained are summarized in Table 1.

COMPARATIVE EXAMPLE 1

A composition (1) was prepared by a method identical with that used in Example 1 and the composition per se was used as a catalyst. Then the properties thereof was evaluated in the same manner used in Example 1. The results obtained are summarized in Table 1.

COMPARATIVE EXAMPLE 2

A composition (2) whose atomic ratio: Cs/Mo was 2/7 was prepared by a method identical with that used in Example 1 and the composition per se was used as a catalyst. Then the properties thereof was evaluated in the same manner used in Example 1. The results obtained are summarized in Table 1.

COMPARATIVE EXAMPLE 3

There were dissolved, in 1200 ml of water, 127.7 g of ammonium paramolybdate and 1.17 g of cesium nitrate under heating and stirring to give a solution (hereinafter referred to as "solution A"). Separately, 139.6 g of cobalt nitrate and 2.2 g of ferric nitrate were dissolved in 180 ml of water to give another solution (hereinafter referred to as "solution B") Further, 28.6 g of bismuth nitrate was dissolved in an aqueous nitric acid solution comprising 15 ml of 60% nitric acid and 150 ml of water to give a solution (hereinafter referred to as "solution C"). Solution B and solution C were, in order, dropwise added to and mixed with solution A, the resulting slurry was spray-dried, then calcined and fired at a temperature of 400° C. to give a catalyst having an atomic ratio: Mo/Bi/Fe/Co/Cs of 12.05/1/3/8/0.1 (the composition thereof was identical to that of the catalyst prepared in Example 1). The properties of the resulting catalyst were evaluated in the same manner used in Example 1. The results obtained are summarized in Table 2.

COMPARATIVE EXAMPLE 4

The same procedures used in Comparative Example 3 were repeated except that the amounts of ammonium paramolybdate and cesium nitrate were changed to 128.3 g and 2.34 g respectively to give a catalyst having an atomic ratio: Mo/Bi/Fe/Co/Cs of 12.1/1/3/8/0.2 (the composition thereof was identical to that of the catalyst prepared in Example 2). The properties of the resulting catalyst were evaluated in the same manner used in Example 1. The results obtained are summarized in Table 2.

COMPARATIVE EXAMPLE 5

The same procedures used in Comparative Example 3 were repeated except that the amounts of ammonium paramolybdate and cesium nitrate were changed to 129.9 g and 5.85 g respectively to give a catalyst having an atomic ratio: Mo/Bi/Fe/Co/Cs of 12.25/1/3/8/0.5 (the composition thereof was identical to that of the catalyst prepared in Example 3). The properties of the resulting catalyst was evaluated in the same manner used in Example 1. The results obtained are summarized in Table 2.

COMPARATIVE EXAMPLE 6

A catalyst was prepared in the same manner disclosed in Example 1 of J.P. KOKAI No. Sho 63-107745. More specifically, 500 parts of ammonium molybdate and 32.2 parts of cesium nitrate were added to 1000 parts of water and then heated and stirred to give a solution A. Separately, 250 parts of 60% nitric acid was added to 850 parts of water, uniformly stirred and then 114.5 parts of bismuth nitrate was added to and dissolved in the solution. Ferric nitrate (286.0 parts) and cobalt nitrate (480.7 parts) were in order added to and dissolved in the resulting solution to give a solution B. After addition of solution B to solution A to give a slurry, 51.6 parts of antimony trioxide having an average particle size of $0.03\mu$ were added and then heated and stirred to evaporate most part of the water. The resulting cake-like substance was dried at 120° C., then calcined at 500° C. for 10 hours and molded into a desired shape to give a catalyst. The properties of the resulting catalyst was evaluated in the same manner used in Example 1. The results obtained are summarized in Table 2.

COMPARATIVE EXAMPLE 7

A catalyst was prepared in the same manner disclosed in Example 1 of J.P. KOKAI No. Sho 63-122642. More specifically, 500 parts of ammonium molybdate, 18.5 parts of ammonium paratungstate, 18.4 parts of cesium nitrate and 354.5 parts of a 20% silica sol were added to 1000 parts of water and then heated and stirred to give a solution A. Separately, 250 parts of 60% nitric acid was added to 850 parts of water, uniformly stirred and then 57.2 parts of bismuth nitrate was added to and dissolved in the solution. Ferric nitrate (238.4 parts), chromium nitrate (4.7 parts), cobalt nitrate (411.8 parts) and magnesium nitrate (60.5 parts) were in order added to and dissolved in the resulting solution to give a solution B. After addition of solution B to solution A to give a slurry, 34.4 parts of antimony trioxide was added and then heated and stirred to evaporate most part of the water. The resulting cake-like substance was dried at 120° C., then calcined at 500° C. for 10 hours and molded into a desired shape to give a catalyst. The properties of the resulting catalyst was evaluated in the same manner used in Example 1. The results obtained are summarized in Table 2.

TABLE 1

| Ex. No. | Composition (2) | Atomic Ratio, A/Bi[1] | Reaction Temp. (°C.) | Conversion (%) | Selectivity (%) | Yield (%) |
|---|---|---|---|---|---|---|
| 1 | $Cs_2MoO_4$ | 0.1 | 340 | 96.2 | 92.7 | 89.2 |
| 2 | $Cs_2MoO_4$ | 0.2 | 340 | 97.0 | 94.1 | 91.3 |
| 3 | $Cs_2MoO_4$ | 0.5 | 360 | 97.4 | 93.8 | 91.4 |
| 4 | $Cs_2Mo_3O_{10}$ | 0.1 | 340 | 94.6 | 92.2 | 87.2 |

TABLE 1-continued

| Ex. No. | Composition (2) | Atomic Ratio, A/Bi[1] | Reaction Temp. (°C.) | Conversion (%) | Selectivity (%) | Yield (%) |
|---|---|---|---|---|---|---|
| 5 | $Cs_2Mo_7O_{22}$ | 0.1 | 340 | 93.8 | 91.8 | 86.1 |
| 6 | $Rb_2MoO_4$ | 0.1 | 340 | 96.6 | 90.9 | 87.8 |
| 7 | $Rb_2Mo_5O_{16}$ | 0.1 | 360 | 98.5 | 91.4 | 90.0 |
| 8 | $K_2MoO_4$ | 0.1 | 340 | 92.9 | 92.3 | 85.7 |
| 9 | $K_2Mo_4O_{13}$ | 0.1 | 360 | 94.7 | 90.8 | 86.0 |
| 10 | $Cs_2MoO_4$ | 0.1 | 340 | 96.8 | 91.4 | 88.5 |
| 11 | $Cs_2MoO_4$ | 0.2 | 340 | 97.5 | 93.8 | 91.5 |
| 12 | $Cs_2MoO_4$ | 0.5 | 360 | 97.8 | 93.3 | 91.2 |
| 13 | $Cs_2MoO_4$ | 1.2 | 400 | 90.1 | 79.3 | 71.4 |
| 1* | — | 0.0 | 360 | 52.2 | 89.5 | 46.7 |
| 2* | $Cs_2Mo_7O_{22}$ | — | 360 | 5.8 | 18.0 | 1.5 |

*Comparative Example
[1])A represents K, Rb or Cs.

In Table 1, "conversion" means the conversion of isobutylene, "selectivity" and "yield" mean the selectivity to methacrolein and the yield thereof.

TABLE 2

| Comp. Ex. No. | Reaction Temp. (°C.) | Conversion (%) | Selectivity (%) | Yield (%) |
|---|---|---|---|---|
| 3 | 340 | 89.5 | 83.2 | 74.5 |
| 4 | 340 | 88.2 | 84.1 | 74.2 |
| 5 | 360 | 90.1 | 82.8 | 74.6 |
| 6 | 340 | 87.2 | 85.1 | 74.2 |
| 7 | 340 | 88.4 | 83.4 | 73.7 |

In Table 2, "conversion" means the conversion of isobutylene, "selectivity" and "yield" mean the selectivity to methacrolein and the yield thereof.

As has been described above in detail, according to the method of the present invention, methacrolein can be prepared in high efficiency by the use of a novel catalyst which is excellent in activity, selectivity to methacrolein and stability.

I claim:

1. A method for preparing methacrolein comprising catalytically oxidizing, in a gas phase, isobutylene or tertiary butanol with molecular oxygen in the presence of a catalyst which comprises a mixture of a composition [1] represented by the following general formula (1):

$$(Mo)_a(Bi)_b(Fe)_c(X)_d(Z)_f(O)_g \quad (1)$$

wherein X represents one or both of Ni and Co, Z represents at least one element selected from the group consisting of W, Be, Mg, S, Ca, Sr, Ba, Te, Se, Ce, Ge, Mn, Zn, Cr, Ag, Sb, Pb, As, B, P, Nb, Cu, Cd, Sn, Al, Zr and Ti, and wherein the ratio of a:b:c:d:f:g is 12:0.1–10:0–20:0–20:0–4 and g is a number of oxygen atoms required for satisfying the valency requirement of the foregoing elements
with a composition (2) represented by the following general formula (2):

$$(A)_m(Mo)_n(O)_p \quad (2)$$

wherein A represents at least one element selected from K, Rb and Cs and wherein the ratio of m:n:p is $2:1-9:3_n+1$, and wherein the mixing ratio of the composition (1) to the composition (2) ranges from 0.02 to 1.0 expressed in terms of the atomic ratio A/Bi and wherein the catalyst is prepared by mixing the composition (1) with the composition (2) with heating at a temperature ranging from 30° to 300° C., evaporating the resulting mixture to dryness at a temperature of not more than 300° C. and then firing the calcined product at a temperature ranging from 300° to 650° C.

2. The method of claim 1 wherein the mixing of the compositions (1) and (2) under heating is carried out in the presence of water.

3. The method according to claim 1 wherein the mixing ratio of the composition (1) to the composition (2) ranges from 0.05 to 0.5 expressed in terms of the atomic ratio A/Bi.

4. The method according to claim 1 further comprising supplying a mixed gas including 1 to 10% by volume of isobutylene of tertiary butanol, 3 to 20% by volume of molecular oxygen, and 70 to 96% by volume of a diluent gas at a temperature ranging from 250° to 450° C., at a pressure ranging from ordinary pressure to 10 atm.

5. The method according to claim 4 further comprising using water vapor with the diluent gas.

6. The method according to claim 1 wherein composition (2) is $Cs_2MoO_4$.

* * * * *